US009743200B2

(12) United States Patent
Farrar et al.

(10) Patent No.: US 9,743,200 B2
(45) Date of Patent: Aug. 22, 2017

(54) MIDDLE EAR IMPLANT SENSOR

(71) Applicant: The Johns Hopkins University, Baltimore, MD (US)

(72) Inventors: Dawnielle Farrar, Randallstown, MD (US); George L. Coles, Jr., Baltimore, MD (US); David A. Kitchin, Laurel, MD (US); Howard W. Francis, Baltimore, MD (US); Ioan Lina, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 729 days.

(21) Appl. No.: 14/260,422

(22) Filed: Apr. 24, 2014

(65) Prior Publication Data

US 2014/0323798 A1 Oct. 30, 2014

Related U.S. Application Data

(60) Provisional application No. 61/817,027, filed on Apr. 29, 2013.

(51) Int. Cl.
*A61F 2/18* (2006.01)
*H04R 25/00* (2006.01)

(52) U.S. Cl.
CPC .......... *H04R 25/606* (2013.01); *H04R 25/30* (2013.01); *H04R 2225/025* (2013.01)

(58) Field of Classification Search
CPC ................................ H04R 25/00; A61F 2/18
USPC ................................ 623/10; 600/25; 607/27
See application file for complete search history.

(56) References Cited

U.S. PATENT DOCUMENTS 8,435,291 B2 5/2013 Wiens et al.

*Primary Examiner* — Yashita Sharma
(74) *Attorney, Agent, or Firm* — Noah J. Hayward

(57) ABSTRACT

A middle ear implant may include a first interface portion configured to interface with a first structure of a middle ear of a patient, a second interface portion configured to interface with a second structure of the middle ear of the patient, a shaft configured to connect the first interface portion and the second interface portion, and a sensor disposed at one end of the shaft, between the shaft and one of the first interface portion or the second interface portion. The sensor may be configured to provide a DC signal output indicative of static pressure on the sensor based on placement of the sensor between the first and second structures. The sensor may also be configured to provide an AC signal output indicative of a frequency response of the implant in response to the sensor being coupled to an output device.

18 Claims, 5 Drawing Sheets

FIG. 3A.
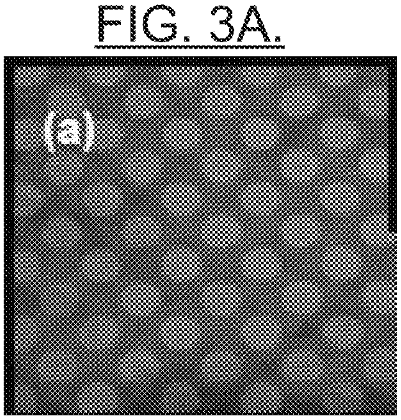
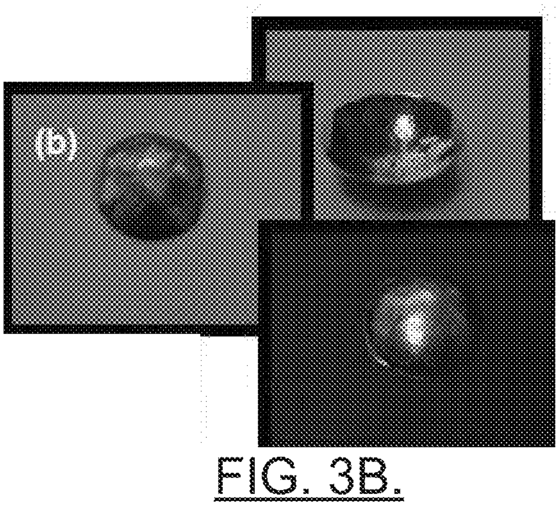
FIG. 3B.
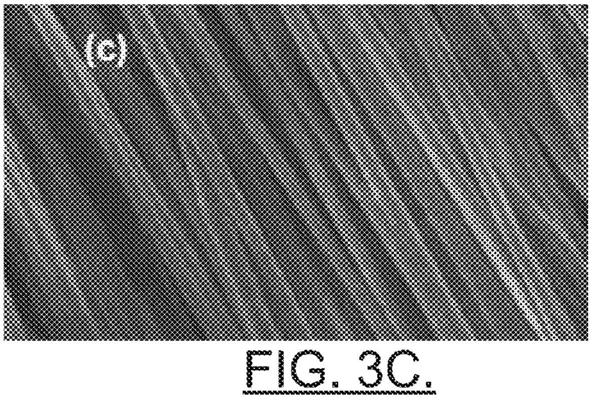
FIG. 3C.

MIDDLE EAR IMPLANT SENSOR

CROSS-REFERENCE TO RELATED APPLICATION

This application claims priority to and the benefit of U.S. Provisional Application Ser. No. 61/817,027 filed on Apr. 29, 2013, the entire contents of which are hereby incorporated herein by reference.

TECHNICAL FIELD

Exemplary embodiments of the present disclosure generally relate to hearing implant technology, and more specifically relate to a sensor that may be used to test the efficacy of a middle ear implant in situ.

BACKGROUND

Over 36 million Americans currently suffer from significant hearing loss. Numerous diseases and traumas can cause conductive hearing loss. Prevalent among these are: Cholesteotoma (bone/joint degeneration of the middle ear bones), mechanical trauma (exposure to exceedingly loud sounds), and barotraumas (exposure to the shock front of an explosive blast or supersonic projectile).

Various types of ear implant surgeries have been developed to facilitate the mitigation or treatment of hearing loss. Some of these surgeries involve the installation of prosthetic implants into the middle ear of patients suffering from hearing loss. In some cases, implant surgeries are conducted and the placement of the prosthesis ends up being less than ideal, so that the implantation surgery needs to be repeated for improved placement. Unfortunately, there are no current long-term criteria in place for evaluation of prosthesis efficacy. Moreover, there are currently no intraoperative measures to predict post-operative prosthesis efficacy. Thus, rates of revision surgery for functional failure have recently been noted as being as high as 18%. However, it is possible that the actual rates at which unsuccessful surgeries are performed could be much higher (e.g., as much as three times higher by some estimates) based on the willingness of some patients to opt out of further surgeries in favor of just dealing with the hearing loss issues.

Accordingly, there is a need to develop an ability to monitor the effective placement of prosthetic implants during the surgical procedures in order to improve outcomes for patients.

BRIEF SUMMARY OF SOME EXAMPLES

Some example embodiments may enable the provision of a system capable of evaluating the installation of a prosthetic implant during the surgical process. In this regard, by embedding a sensor into the implant, example embodiments may enable the installation of some implants to be monitored for such things as, for example, proper adjustment and positioning. Rather than waiting for months after surgery to obtain audiology reports, surgeons may be able to monitor installation and expected response parameters based on the current situation and provide better installation results.

In one example embodiment, a middle ear implant is provided. The middle ear implant may include a first interface portion configured to interface with a first structure of a middle ear of a patient, a second interface portion configured to interface with a second structure of the middle ear of the patient, a shaft configured to connect the first interface portion and the second interface portion, and a sensor disposed at one end of the shaft, between the shaft and one of the first interface portion or the second interface portion. The sensor may be configured to provide a DC signal output indicative of static pressure on the sensor based on placement of the sensor between the first and second structures. The sensor may also be configured to provide an AC signal output indicative of a frequency response of the implant in response to the sensor being coupled to an output device.

In another example embodiment, a test set is provided. The test set may include a meter and a middle ear implant. The middle ear implant may include a first interface portion configured to interface with a first structure of a middle ear of a patient, a second interface portion configured to interface with a second structure of the middle ear of the patient, a shaft configured to connect the first interface portion and the second interface portion, and a sensor disposed at one end of the shaft, between the shaft and one of the first interface portion or the second interface portion. The sensor may be configured to provide a DC signal output indicative of static pressure on the sensor based on placement of the sensor between the first and second structures. The sensor may also be configured to provide an AC signal output indicative of a frequency response of the implant in response to the sensor being coupled to an output device. The meter may be configured to interface with the sensor during the surgical procedure to provide indications to an operator regarding the DC and AC signal outputs.

In still another example embodiment, a method of employing a sensor for providing feedback on implant placement during surgical procedures for a middle ear implant is provided. The method may include placing the sensor comprising top and bottom electrodes within a portion of the implant, providing electrical leads to interface with the top and bottom electrodes at a top surface and a bottom surface, respectively, of the sensor and attaching the electrical leads to a meter, placing the implant in the middle ear of a patient, detecting a DC component at the meter indicative of static pressure placed on the sensor based on its placement in the middle ear, detecting an AC component at the meter indicative of frequency response of the implant, and removing the electrical leads and leaving the sensor within the implant in an isolated state.

BRIEF DESCRIPTION OF THE SEVERAL VIEWS OF THE DRAWING(S)

Having thus described some example embodiments of the invention in general terms, reference will now be made to the accompanying drawings, which are not necessarily drawn to scale, and wherein:

FIG. 3A illustrates a patterned piezoelectric composite film as a polymer sheet in accordance with an example embodiment;

FIG. 3B illustrates a contoured/dome-shaped polymer sheet with different possible shapes that may be employed in accordance with an example embodiment;

FIG. 3C illustrates a sensor layer formed from a bundled series of piezoelectric nanofibers in accordance with an example embodiment;

DETAILED DESCRIPTION

Figure 1:
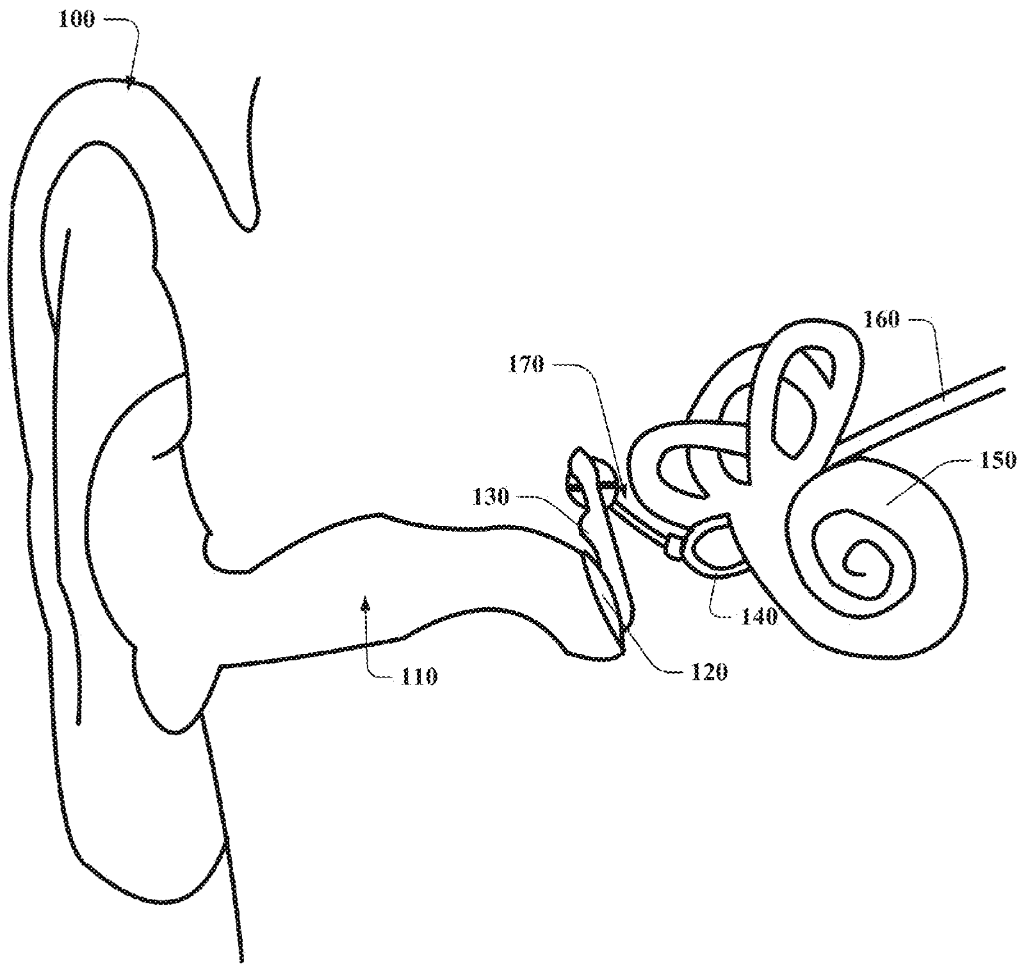
FIG. 1 illustrates a conceptual view of the middle ear of a patient employing an implant device in accordance with an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

A sensor, and corresponding system, for evaluating the installation of a prosthetic implant during the surgical process is provided. In this regard, the sensor can be provided within a portion of the implant to enable proper adjustment and positioning to be monitored. In some cases, the sensor can be provided within a portion of the implant and can be tested during the surgical procedure to measure both the load on the implant and the frequency response of the implant. Accordingly, for example, surgeons may be able to test and adjust, if needed, during installation. As such, response parameters and loading may be monitored during installation so that provide better installation results can be achieved without waiting for months after surgery to obtain audiology reports. The sensor is therefore configured to provide real-time data indicative of output parameters generated based on placement of the implant in the middle ear during a surgical procedure so that adjustments can be made as necessary to improve placement for better likelihood of successful hearing loss mitigation.

FIG. 1 illustrates a conceptual view of the middle ear of a patient employing a device in accordance with an example embodiment. In this regard, as shown in FIG. 1, an outer ear 100 and ear canal 110 may direct sound energy in toward the ear drum 120. Movement at the ear drum 120 may be transferred to the malleus 130 (or hammer). Normally, the malleus 130 may transfer sound energy to the incus (or anvil—not shown), which further transfers the sound energy to the stapes (or stirrup) 140. From the stapes 140, sound energy is transferred to the chochlea 150 or inner ear, where the sound pressure patterns are converted to electrical impulses that can be transmitted to the brain via the auditory nerve 160.

In cases where a bone of the inner ear (i.e., the malleus 130, incus or stapes 140) is non-functional (or at least functioning improperly) due to disease, damage or defect, it may be possible to replace the corresponding bone (or bones) with a prosthetic implant. Such an implant may generally be provided to function in a similar manner to the bone that is to be replaced. In the present example, the incus may have been missing, damaged or otherwise non-functional and a prosthesis (or implant 170) may be provided to bridge the distance between the malleus 130 and the stapes 140. The implant 170 may be surgically installed between the malleus 130 and the stapes 140 and placed under load due to the pressure between the malleus 130 and the stapes 140.

The mere replacement of a damaged incus with the implant 170 may be performed substantially using conventional techniques. However, in accordance with an example embodiment, the implant 170 may have sensor technology employed therein that may enable the loading and frequency response of the implant 170 to be monitored prior to completion of the installation surgical procedure. The sensor technology may enable the surgeon to have the loading checked to determine whether it falls within an acceptable range, and may allow a stimulus to be applied to the implant 170 so that frequency response of the implant 170 may be monitored, again relative to acceptable levels. In an example embodiment, the sensor installed with the implant 170 may generate a voltage proportional to the compression force between the malleus 130 and the stapes 140. The voltage may be measured to enable the positioning of the implant 170 to be optimized. Additionally, acoustic transmission characteristics may be evaluated prior to completing the implantation surgery.

It should be appreciated that although a particular implant (i.e., implant 170) for replacement of the incus is described herein, example embodiments may also be used in connection with other specific implants where the design features described herein remain applicable. Thus, the images and descriptions provided herein should be appreciated as being provided for purposes of enabling the description of an example and not for purposes of limitation.

Figure 2A:
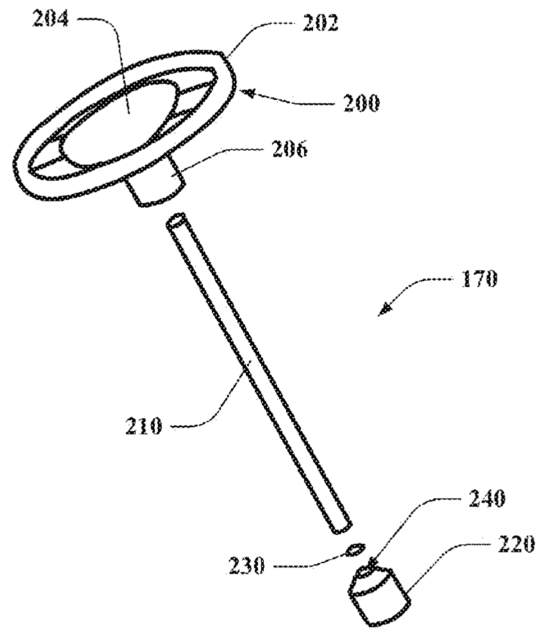
FIG. 2A illustrates an exploded, perspective view of the implant in accordance with an example embodiment.
Figure 2B:
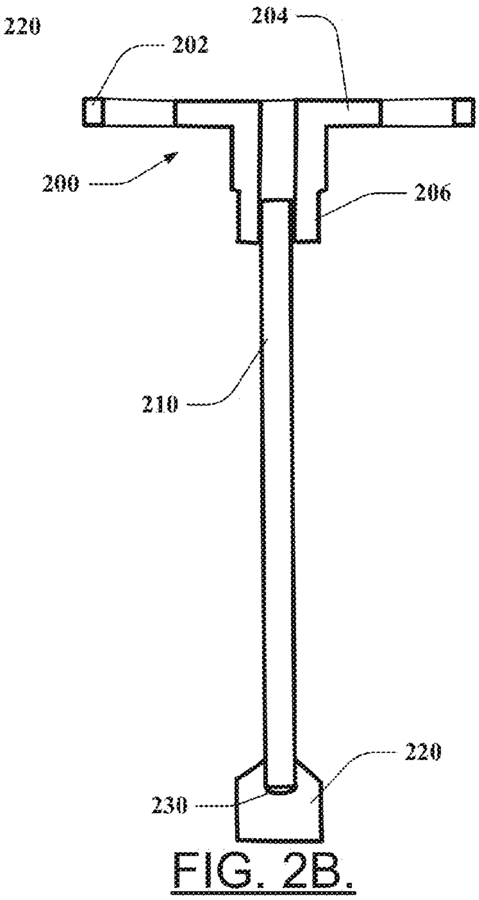
FIG. 2B illustrates a cross sectional view of the implant in accordance with an example embodiment.

FIG. 2, which includes FIGS. 2A and 2B, illustrates the implant 170 of an example embodiment in greater detail. In this regard, FIG. 2A illustrates an exploded, perspective view of the implant 170 in accordance with an example embodiment. Meanwhile, FIG. 2B illustrates a cross sectional view of the implant 170 in accordance with an example embodiment. Referring to FIGS. 2A and 2B, the implant 170 may include first interface portion 200, a shaft 210 and a second interface portion 220. The implant 170 may also include a sensor 230 that may be provided between the shaft 210 and the second interface portion 220. It should be appreciated, however, that the sensor 230 could alternatively be located between the first interface portion 200 and the shaft 210 or at any other suitable location of a differently structured implant.

The first and second interface portions 200 and 220 may be structured in any suitable fashion. However, given that the implant 170 of this example embodiment replaces the incus, the first interface portion 200 may be somewhat larger and have a disc shape to facilitate interfacing with the malleus 130 over a relatively larger surface area, while the second interface portion 220 has a cylindrical shaped terminus to facilitate interfacing with the stapes 140 over a relatively smaller surface area. In an example embodiment, the first interface portion 200 may be formed of an annular portion 202 that extends around a disc portion 204 to facilitate expanding the surface area of the first interface portion 200. In some cases, one or more axial support members may extend axially outward from the disc portion 204 to engage and hold the annular portion 202 so that the disc portion 204, the annular portion 202 and any axial support members are substantially coplanar within a plane that lies substantially perpendicular to the direction of extension of the shaft 210. The disc portion 204 may further include a receiving portion 206 that may extend around a portion of the shaft 210 to receive the shaft 210. As such, the receiving portion 206 may form or include a hollow cylinder extending in the direction of extension of the shaft 210 to receive a proximal end of the shaft 210 within the hollow cylinder of the receiving portion 206.

The shaft 210 may extend away from a center of the disc portion 204 and, in some cases, may define an axial centerline of the disc portion 204. The shaft 210 may extend toward the second interface portion 220 and a distal end of the shaft 210 may terminate in the second interface portion 220. As shown in FIG. 2, the second interface portion 220 may include a receiving opening 240 configured to receive the distal end of the shaft 210. Thus, the shaft 210, which may have a cylindrical shape, may be received within a cylindrically shaped orifice formed in the second interface portion 220, and forming the receiving opening 240. However, it should be appreciated that any corresponding shapes could be employed in alternative embodiments.

The sensor 230 may be provided at a floor of the receiving opening 240 so that when the shaft 210 is seated within the receiving opening 240, the sensor 230 is enclosed within the assembled combination of the shaft 210 and the second interface portion 220. As such, the sensor 230 may be arranged to lie in a plane that is substantially perpendicular to the direction of extension of the shaft 210 and substantially parallel to the plane in which the disc portion 204, the annular portion 202 and any axial support members of the first interface portion 200 may lie.

In an example embodiment, the first and second interface portions 200 and 220 and the shaft 210 may be made of a rigid material that is suitable for long term insertion into the human body without adverse affects. The insertion area into which the implant 170 is provided is often as small as 3 mm, thus, the material must be capable of being machined, molded or otherwise produced with great accuracy at a relatively small size. In some cases, Titanium may be employed as a material of which some or all of the components of the implant 170 may be made. However, alternative metals or composite materials are also candidates for use, and it is not necessarily required that all portions of the implant 170 be made from the same material.

The sensor 230 may be formed of a sheet or mat of material having a relatively thin depth dimension. For example, some example embodiments may employ a film or fiber structure having a thickness of about 40 microns. In some embodiments, the sensor 230 may be embodied as a piezoelectric Poly(γ-benzyl α, L-glutamate) (PBLG) film or fiber sensor that forms a sensing layer that can be inserted into the floor of the receiving opening 240. Any force transmitted along the shaft 210 may then be sensed at the sensing layer forming the sensor 230. In some embodiments, the sensing layer may be formed using piezoelectric nanofibers, as a patterned piezoelectric composite film, or as a contoured/dome-shaped sample.

FIG. 3, which includes FIGS. 3A, 3B and 3C, illustrates examples of images that may form a film or fiber sheet for formation of the sensor layer. In this regard, FIG. 3A illustrates a patterned piezoelectric composite film as a polymer sheet. FIG. 3B illustrates a contoured/dome-shaped polymer sheet with different possible shapes that may be employed in accordance with an example embodiment. FIG. 3C illustrates a sensor layer formed from a bundled series of piezoelectric nanofibers. Such materials may be polymer based materials that are generally polar in nature, and the dipoles of such materials may be controlled during the manufacturing process to optimize the materials for providing electrical signals in response to mechanical stimuli. By providing an electrical contact (e.g., an electrode) on each of the top and bottom surfaces of the sensor layer forming the sensor 230, electrical impulses generated responsive to the load imparted through the shaft 210 can be detected and measured across the sensor 230 using, for example, a charge or displacement meter.

In an example embodiment, the sensor 230 may therefore be formed of an active sensing material that can generate electrical impulses based on mechanical stimuli. However, the primary function of the sensor 230 may be to provide feedback on implant 170 placement during a surgical procedure, and the sensor 230 may therefore essentially cease to function after the surgical procedure is completed. As such, the sensor 230 may be integrated as part of a testing system with electrical leads attached to the electrodes on the top and bottom of the sensor layer forming the sensor material 230 at some point during the surgical procedure. However, the electrical leads may be removed from contact with the electrodes and the sensor 230 may then remain dormant within the implant 170 thereafter. Due to the relatively thin nature of the sensor 230, and the fact that the sensor 230 lies at the floor of the receiving opening 240, the shaft 210 and the second interface portion 220 may combine to completely enclose the sensor 230 after the electrical leads are removed so that the sensor 230 does not impact the operation of the implant 170 and also does not interact with the environment in which the implant 170 is located.

Figure 4:
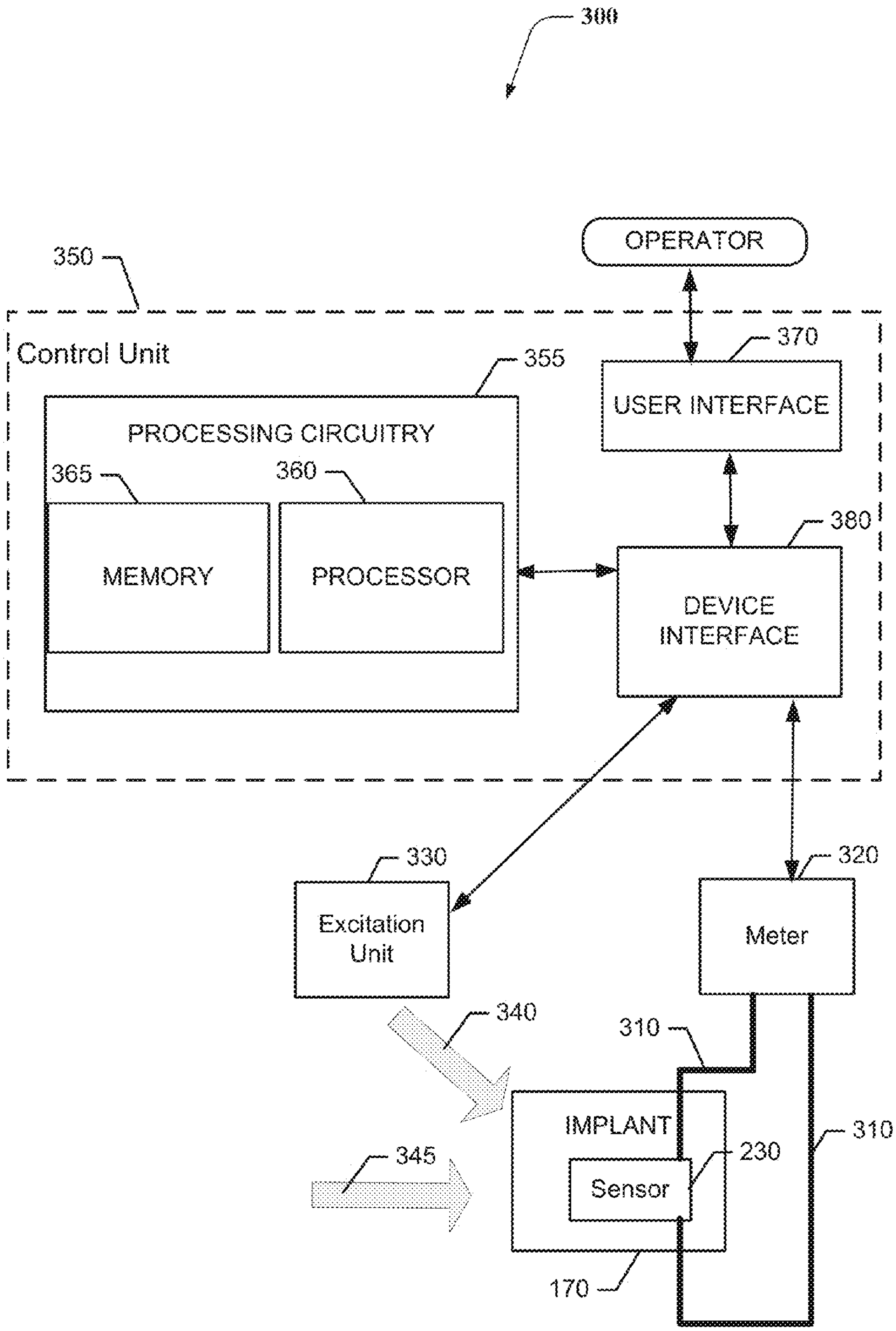
FIG. 4 illustrates a block diagram of a test set for use while installing the implant in accordance with an example embodiment.

FIG. 4 illustrates a block diagram of a test set 300 for use while installing the implant 170 in accordance with an example embodiment. As shown in FIG. 4, the test set 300 may include the sensor 230 placed in the implant 170. Electrical leads 310 may be in communication with top and bottom sides, respectively, of the sensor layer forming the sensor 230. The electrical leads 310 may be provided to a meter 320 configured to monitor electrical signals generated by the sensor 230. In some cases, the test set 300 may further include an excitation unit 330 that may be configured to generate one or more test signals 340 that can be introduced to the middle ear of the patient in order to monitor the response to the test signals 340 at the sensor 230 via the meter 320.

In an example embodiment, a control unit 350 may further be provided to control and/or coordinate operation of the test set 300. As such, for example, the control unit 350 may be used to enable the operator to control application of and/or define parameters of the test signals 340. The control unit 350 may also or alternatively monitor outputs detected at the meter 320 and conduct analysis of the outputs to enable the surgeon or other operator to determine whether the output parameters sensed at the sensor 230 (i.e., the electrical impulses detected in response to the mechanical input provided by in the form of the test signals) are within acceptable ranges for the test signals 340 provided.

As such, for example, the test signals 340 may be one or more sound inputs that may have known parameters or characteristics, and the control unit 350 may store data indicative of an acceptable range of output parameters for given input parameters. The output parameters may include an AC signal indicative of frequency response characteristics of the implant 170 based on its present location. Meanwhile, the pressure or static load 345 placed upon the implant 170 by the bones or other features between which the implant 170 is placed may also generate an electrical impulse. The output generated based on the static load 345 may be represented as a DC signal indicative of the pressure load between the bones that the implant 170 contacts.

The control unit 350 may include processing circuitry 355 configured to execute instructions for control of the excitation unit 330 and/or for analysis of the output parameters detected at the meter 320. The processing circuitry 355 may be configured to perform data processing, control function execution and/or other processing and management services according to an example embodiment of the present invention. In some embodiments, the processing circuitry 355 may be embodied as a chip or chip set. In other words, the processing circuitry 355 may comprise one or more physical packages (e.g., chips) including materials, components and/or wires on a structural assembly (e.g., a baseboard).

In an example embodiment, the processing circuitry 355 may include one or more instances of a processor 360 and memory 365 that may be in communication with or otherwise control a device interface. As such, the processing circuitry 355 may be embodied as a circuit chip (e.g., an integrated circuit chip) configured (e.g., with hardware, software or a combination of hardware and software) to perform operations described herein. The processing circuitry 355 may further interface with a user interface 370 and/or a device interface 380 of the control unit 350.

The device interface 380 may include one or more interface mechanisms for enabling communication with other external devices (e.g., output devices, input devices, and/or the like) or the modules/components of the test set 300. In some cases, the device interface 380 may be any means such as a device or circuitry embodied in either hardware, or a combination of hardware and software that is configured to receive and/or transmit data from/to devices and/or modules in communication with the processing circuitry 355. Thus, the device interface 380 may enable the processor 360 to communicate with the excitation unit 330 and/or the meter 320.

In an exemplary embodiment, the memory 365 may include one or more non-transitory memory devices such as, for example, volatile and/or non-volatile memory that may be either fixed or removable. The memory 365 may be configured to store information, data, applications, instructions or the like for enabling the processing circuitry 355 to carry out various functions in accordance with exemplary embodiments of the present invention. For example, the memory 365 could be configured to buffer input data for processing by the processor 360. Additionally or alternatively, the memory 365 could be configured to store instructions for execution by the processor 360. As yet another alternative, the memory 365 may include one or more databases that may store a variety of excitation patterns and/or data sets indicative of specific test signals 340 for input and corresponding acceptable output parameters and/or acceptable static load parameters that may be employed for the execution of example embodiments. Among the contents of the memory 365, applications may be stored for execution by the processor 360 in order to carry out the functionality associated with each respective application. In some cases, the applications may include directions for control of the excitation unit 330 and/or processing and analysis of data received at the meter 320 so that an output can be provided to the operator at the user interface 370.

The processor 360 may be embodied in a number of different ways. For example, the processor 360 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 360 may be configured to execute instructions stored in the memory 365 or otherwise accessible to the processor 360. As such, whether configured by hardware or by a combination of hardware and software, the processor 360 may represent an entity (e.g., physically embodied in circuitry—in the form of processing circuitry 355) capable of performing operations according to embodiments of the present invention while configured accordingly. Thus, for example, when the processor 360 is embodied as an ASIC, FPGA or the like, the processor 360 may be specifically configured hardware for conducting the operations described herein. Alternatively, as another example, when the processor 360 is embodied as an executor of software instructions, the instructions may specifically configure the processor 360 (which could in some cases otherwise be a general purpose processor) to perform the operations described herein.

In an example embodiment, the processor 360 (or the processing circuitry 355) may be embodied as, include or otherwise control the modules of the control unit 350. As such, in some embodiments, the processor 360 (or the processing circuitry 355) may be said to cause each of the operations described in connection with the modules of the control unit 350 to undertake the corresponding functionalities responsive to execution of instructions or algorithms configuring the processor 360 (or processing circuitry 355) accordingly.

The user interface 370 (if implemented) may be in communication with the processing circuitry 355 to receive an indication of a user input at the user interface 370 and/or to provide an audible, visual, mechanical or other output to the user. As such, the user interface 370 may include, for example, a display, printer, one or more buttons or keys (e.g., function buttons), and/or other input/output mechanisms (e.g., keyboard, touch screen, mouse, microphone, speakers, cursor, joystick, lights and/or the like). The user interface 370 may display information regarding control unit 350 operation. The information may then be processed and further information associated therewith may be presented on a display of the user interface 370 based on instructions executed by the processing circuitry 355 for the analysis of the data according to prescribed methodologies and/or algorithms. Moreover, in some cases, the user interface 370 may include options for selection of one or more reports to be generated based on the analysis of a given data set. Interface options (e.g., selectable instructions, or mechanisms by which to define instructions) may also be provided to the operator using the user interface 370.

As mentioned above, the test set 300 may be employed during an operation to enable the operator to adjust the location or placement of the implant 170 based on output parameters detected at the meter 320. In this regard, the static load 345 may generate a DC signal output from the sensor 230 that may be observable by the operator at the meter 320 itself (or at the user interface 370). The operator may compare the DC signal output to acceptable ranges defined based on trial data for patients having similar physical characteristics as the patient (e.g., based on gender, age, height, or other applicable profile data). After the placement of the implant 170 is validated using DC signal output data generated based on the static load 345, the operator may then provide an excitation (e.g., the test signals 340) and monitor the output parameters in the form of an indication of the frequency response provided by the implant based on its current location or placement. If the frequency response is also within acceptable levels, the operator may determine that the current location or placement of the implant 170 is within acceptable parameters and conclude the surgical operation. The data associated with conclusion of this particular operation may also be recorded so that the outcomes for the patient can be evaluated and, over time, trend analysis may confirm existing acceptable ranges or the acceptable ranges can be modified.

Figure 5:
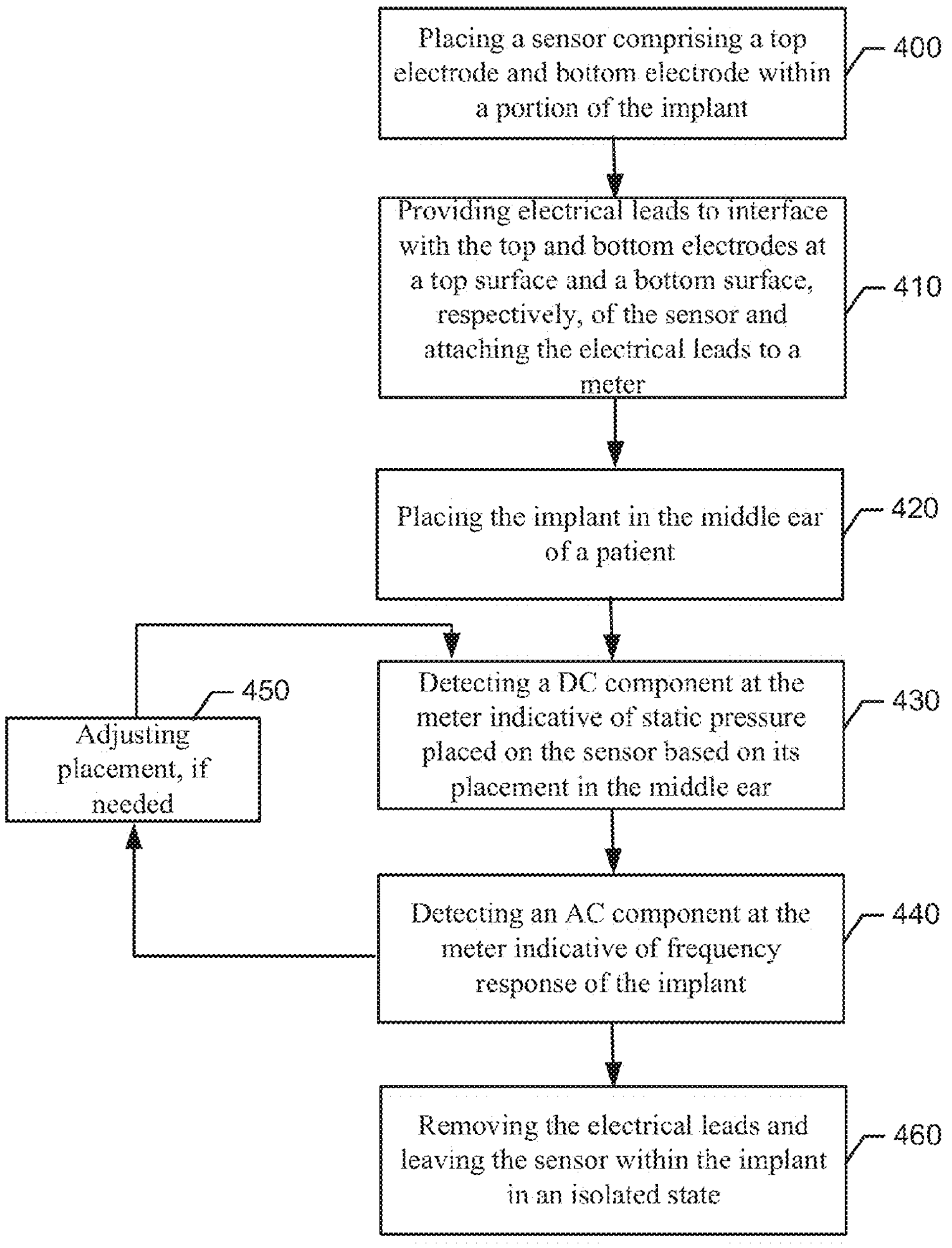
FIG. 5 illustrates a block diagram of a method of employing a sensor for providing feedback on implant placement during surgical procedures for a middle ear implant in accordance with an example embodiment.

FIG. 5 illustrates a block diagram of a method of employing a sensor for providing feedback on implant placement during surgical procedures for a middle ear implant in accordance with an example embodiment. The method may include placing a sensor comprising top and bottom electrodes within a portion of the implant or prosthetic at operation 400. The method may further include providing electrical leads to interface with the top electrode and the bottom electrode disposed at a top surface and bottom surface, respectively, of the sensor and attaching the electrical leads to a meter at operation 410. At operation 420, the implant may be placed in the middle ear of a patient. At operation 430, a DC component may be detected at the meter indicative of static pressure placed on the sensor based on its placement in the middle ear. An AC component indicative of frequency response of the implant may then be detected by the meter at operation 440. Any needed adjustments to implant location may be performed at operation 450 and the AC and/or DC components may be rechecked as appropriate. At operation 460, the electrical leads may be removed and the sensor may be left within the implant in an isolated state.

Example embodiments therefore represent a design for a middle ear implant and corresponding test set for use with the implant. The middle ear implant may include a first interface portion configured to interface with a first structure of a middle ear of a patient, a second interface portion configured to interface with a second structure of the middle ear of the patient, a shaft configured to connect the first interface portion and the second interface portion, and a sensor disposed at one end of the shaft, between the shaft and one of the first interface portion or the second interface portion. The sensor may be configured to provide a DC signal output indicative of static pressure on the sensor based on placement of the sensor between the first and second structures. The sensor may also be configured to provide an AC signal output indicative of a frequency response of the implant in response to the sensor being coupled to an output device. The test set may include the implant and a meter where the meter is configured to interface with the sensor during the surgical procedure to provide indications to an operator regarding the DC and AC signal outputs. By embedding the sensor in the implant, verification of optimal implant compression (e.g., between the malleus and stapes) and likelihood of hearing restoration (e.g., within 0-20 dB across the frequency range of speech) may be conducted during surgery. The real-time feedback provided via the sensor may enable the surgeon to verify proper adjustment and positioning of the implant during surgery instead of weeks or months later. Example embodiments may also enable training procedures to be conducted and monitored based on simulating environmental conditions and monitoring surgeon performance relative to setting the implant in proper location for simulated conditions.

In some embodiments, additional optional structures and/or features may be included or the structures/features described above may be modified or augmented. Each of the additional features, structures, modifications or augmentations may be practiced in combination with the structures/features above and/or in combination with each other. Thus, some, all or none of the additional features, structures, modifications or augmentations may be utilized in some embodiments. Some example additional optional features, structures, modifications or augmentations are described below, and may include, for example, installing the implant such that the first structure is a malleus and the second structure is a stapes of the patient. Alternatively or additionally, some embodiments may include the sensor being disposed at a floor of a receiving opening formed in the second interface portion to receive mechanical forces imparted on the shaft. Alternatively or additionally, some embodiments may include the sensor being embodied as a sensing layer configured to have a first electrical lead contact a top surface of the sensing layer and a second electrical lead contact a bottom surface of the sensing layer to generate electrical impulses based on the mechanical forces imparted on the shaft. In some cases, the sensor layer may be formed from a patterned piezoelectric composite film provided as a polymer sheet, a contoured/dome-shaped polymer sheet, or a sensor layer formed from a bundled series of piezoelectric nanofibers. In an example embodiment, the first and second electrical leads may be removed prior to completing a surgical procedure during which the implant is placed in the middle ear of the patient, and the sensor may remain in the implant in an isolated state. Additionally or alternatively, the sensor may be configured to provide real-time data indicative of output parameters generated based on placement of the implant in the middle ear during a surgical procedure. Additionally or alternatively, the test set may further include an excitation unit configured to provide test signals for stimulating and evaluation of the AC signal output. Additionally or alternatively, the test set may further include a control unit configured to control the excitation unit and the meter. Additionally or alternatively, the control unit comprises a user interface configured to enable the operator to define stimuli for evaluation. Additionally or alternatively, the control unit may include processing circuitry configured to evaluate the AC signal output and/or DC signal output relative to respective predefined ranges to determine whether the placement of the implant results in the AC signal output and/or the DC signal output being within the respective predefined ranges.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A middle ear implant comprising:

a first interface portion configured to interface with a first structure of a middle ear of a patient;

a second interface portion configured to interface with a second structure of the middle ear of the patient;

a rigid shaft configured to connect the first interface portion and the second interface portion; and a sensor disposed at one end of the rigid shaft, between the rigid shaft and one of the first interface portion or the second interface portion, the sensor being configured to provide a DC signal output indicative of static pressure on the sensor based on placement of the sensor between the first and second structures, and provide an AC signal output indicative of a frequency response of the implant in response to the sensor being coupled to an output device.

2. The middle ear implant of claim 1, wherein the first structure comprises a malleus and the second structure comprises a stapes of the patient.

3. The middle ear implant of claim 1, wherein the sensor is disposed at a floor of a receiving opening formed in the second interface portion to receive mechanical forces imparted on the rigid shaft.

4. The middle ear implant of claim 3, wherein the sensor comprises a sensing layer configured to have a first electrical lead contact a top surface of the sensing layer and a second electrical lead contact a bottom surface of the sensing layer to generate electrical impulses based on the mechanical forces imparted on the rigid shaft.

5. The middle ear implant of claim 4, wherein the sensor layer is formed from:

patterned piezoelectric composite film provided as a polymer sheet;

a contoured/dome-shaped polymer sheet; or a sensor layer formed from a bundled series of piezoelectric nanofibers.

6. The middle ear implant of claim 4, wherein the first and second electrical leads are removed prior to completing a surgical procedure during which the implant is placed in the middle ear of the patient, and wherein the sensor remains in the implant in an isolated state.

7. The middle ear implant of claim 1, wherein the sensor is configured to provide real-time data indicative of output parameters generated based on placement of the implant in the middle ear during a surgical procedure.

8. A test set for monitoring a surgical procedure, the test set comprising:

a meter; and a middle ear implant comprising:

a first interface portion configured to interface with a first structure of a middle ear of a patient;

a second interface portion configured to interface with a second structure of the middle ear of the patient;

a rigid shaft configured to connect the first interface portion and the second interface portion; and a sensor disposed at one end of the rigid shaft, between the rigid shaft and one of the first interface portion or the second interface portion, the sensor being configured to provide a DC signal output indicative of static pressure on the sensor based on placement of the sensor between the first and second structures, and provide an AC signal output indicative of a frequency response of the implant in response to the sensor being coupled to an output device, wherein the meter is configured to interface with the sensor during the surgical procedure to provide indications to an operator regarding the DC and AC signal outputs.

9. The test set of claim 8, wherein the first structure comprises a malleus and the second structure comprises a stapes of the patient.

10. The test set of claim 8, wherein the sensor is disposed at a floor of a receiving opening formed in the second interface portion to receive mechanical forces imparted on the rigid shaft.

11. The test set of claim 10, wherein the sensor comprises a sensing layer configured to have a first electrical lead contact a top surface of the sensing layer and a second electrical lead contact a bottom surface of the sensing layer to generate electrical impulses based on the mechanical forces imparted on the rigid shaft.

12. The test set of claim 11, wherein the sensor layer is formed from:

patterned piezoelectric composite film provided as a polymer sheet;

a contoured/dome-shaped polymer sheet; or a sensor layer formed from a bundled series of piezoelectric nanofibers.

13. The test set of claim 11, wherein the first and second electrical leads are removed prior to completing a surgical procedure during which the implant is placed in the middle ear of the patient, and wherein the sensor remains in the implant in an isolated state.

14. The test set of claim 8, wherein the sensor is configured to provide real-time data indicative of output parameters generated based on placement of the implant in the middle ear during a surgical procedure.

15. The test set of claim 8, further comprising an excitation unit configured to provide test signals for stimulating and evaluation of the AC signal output.

16. The test set of claim 15, further comprising a control unit configured to control the excitation unit and the meter.

17. The test set of claim 16, wherein the control unit comprises a user interface configured to enable the operator to define stimuli for evaluation.

18. The test set of claim 16, wherein the control unit comprises a processing circuitry configured to evaluate the AC signal output and/or DC signal output relative to respective predefined ranges to determine whether the placement of the implant results in the AC signal output and/or the DC signal output being within the respective predefined ranges.

* * * * *